United States Patent
Chen et al.

(10) Patent No.: US 7,138,540 B1
(45) Date of Patent: Nov. 21, 2006

(54) CONVENIENT METHOD FOR THE PREPARATION OF NEW PRECURSOR OF NO-CARRIER-ADDED O-(2-[18F]FLUOROETHYL)-L-TYROSINE)

(75) Inventors: Jenn Tzong Chen, Taoyuan (TW); Wuu Jyh Lin, Taoyuan (TW); Ai Ren Lo, Taoyuan (TW); Ming Hsin Lee, Taoyuan (TW); Hsin Er Wang, Taoyuan (TW); Shih Yan Wu, Taoyuan (TW)

(73) Assignee: Institute of Nuclear Energy Research, Taoyuan (TW)

( * ) Notice: Subject to any disclaimer, the term of this patent is extended or adjusted under 35 U.S.C. 154(b) by 0 days.

(21) Appl. No.: 11/162,287

(22) Filed: Sep. 6, 2005

(51) Int. Cl.
*C07C 229/36* (2006.01)

(52) U.S. Cl. .................................................. 560/27
(58) Field of Classification Search ................. 560/27
See application file for complete search history.

(56) References Cited

U.S. PATENT DOCUMENTS 6,451,835 B1   9/2002   Dekeyser .................... 514/406

OTHER PUBLICATIONS

Hamacher, et al. Efficient routine production oc the 18F-labelled amino acid O-(2-[18F]fluoroethyl)-L-tyrosine. Applied Radiation and Isotopes, 2002, 57, 853-856.*

* cited by examiner

*Primary Examiner*—Kamal A. Saeed
*Assistant Examiner*—Shawquia Young
(74) *Attorney, Agent, or Firm*—Pai Patent & Trademark Law Firm; Chao-Chang David Pai

(57) ABSTRACT

This is a new precursor and new method for the synthesis of no-carrier-added O-(2-[$^{18}$F]fluoroethyl)-L-Tyrosine which has been proved a suitable PET (position emission tomography) probe for tumor diagnosis imaging, the preparation of the title compound starts from precursors with the chemical structures as in Formula 1, wherein $R^1$ is a protective group for the carboxyl functional group, $R^2$ is a protective group for the amino group, and $R^3$ acts as a leaving group. $R^1$ represents an arylalkyl group, $R^2$ represents a carboxyl group, and $R^3$ represents a p-tosyloxy, methane sulfonyloxy or trifluoromethane sulfonyloxy or bromine, the invention includes a method for the syntheses of new precursors with the chemical structures as in Formula 1.

1 Claim, No Drawings

CONVENIENT METHOD FOR THE PREPARATION OF NEW PRECURSOR OF NO-CARRIER-ADDED O-(2-[18F]FLUOROETHYL)-L-TYROSINE)

BACKGROUND OF THE INVENTION

[18F]-labeled O-(2-[$^{18}$F]fluoroethyl)-L-Tyrosine is an amino acid tracer, it has been proved as a suitable PET (position emission tomography) probe for tumor diagnosis imaging.

The preparation of O-(2-[$^{18}$F]fluoroethyl)-L-Tyrosine was developed by Wester et al. (J. Nucl. Med. 1999; 40:205–212) and Hamacher et al. (Appl. Radiat. Isot. 2002; 57:853–856). However, it is inconvenient by using high performance liquid chromatography (HPLC) for purified product, it is not only cumbersome but also difficult automation, since during HPLC purify process operator must switch valve from waste collecting bottle to product bottle in order to collect purified O-(2-[$^{18}$F]fluoroethyl)-L-Tyrosine and switch valve back to waste bottle after complete the collection of purified product in order to maintain high purified O-(2-[$^{18}$F]fluoroethyl)-L-Tyrosine. The present invention provides a new precursor for smooth synthesis, and utilizes resin and silica gel column for purification to reduce complexity of HPLC purification process.

CITED REFERENCES

H. I. Wester, M. Herz, W. Weber, P. Heiss, R. Senekowitsch-Schmidtke, M. Schwaiger and G. Stöcklin, Synthesis and radiopharmacology of O-(2-[$^{18}$F]fluoroethyl)-L-Tyrosine for tumor imaging. J. Nucl. Med. 40, 205–212 (1999).

K. Hamacher and H. H. Coenen, Efficient routine production of the $^{18}$F-labelled amino acid O-(2-[$^{18}$F]fluoroethyl)-L-Tyrosine, Appl. Radiat. Isot. 57, 853–856 (2002).

SUMMARY OF THE INVENTION

The object of this invention provides a synthetic method of novel t-BOC-(O-tosyloxyethyl)-L-Tyr-OBzl (as Formula 1), which is a precursor of O-(2-[$^{18}$F]fluoroethyl)-L-Tyrosine.

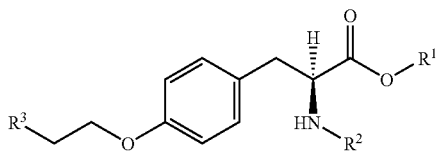

Formula 1: Synthesis precursors for O-(2-[$^{18}$F]fluoroethyl)-L-Tyrosine.

For the synthesis of O-(2-[$^{18}$F]fluoroethyl)-L-Tyrosine, the initial labeled-compound (that is precursor) is prepared above all. This synthesis procedure is carried out in chemistry lab instead of in radiation control area because of no radiation.

Precursor of O-(2-[$^{18}$F]fluoroethyl)-L-Tyrosine

Synthesis of O-(2-[$^{18}$F]fluoroethyl)-L-Tyrosine: (1) Prepare ethylene glycol-1,2-ditosylate. React ethylene glycol and toluenesulfonyl chloride in pyridine solution at low temperature for two to three days, warming the solution, solidify the product and purify by re-crystallization to obtain ethylene glycol-1,2-ditosylate. (2) Prepare t-Boc-(O-tosyloxyethyl)-L-Tyr-Obzl. Add t-Boc-L-Tyr-OBzl in acrylonitrile solution contains ethylene glycol-1,2-ditosylate and potassium carbonate, heat to 90° C. in stirring for react four hours, remove solvent after complete the reaction, then extract with chloroform to obtain solid residue, purify dissolved residue by column chromatography and obtain pure t-Boc-(O-tosyloxyethyl)-L-Tyr-OBzl product.

DETAILED DESCRIPTION OF THE INVENTION

The embodiments of the invention will be described as follows:

The synthetic method of $^{18}$F-labeled precursor t-BOC-(O-tosyloxyethyl)-L-Tyr-OBzl

1. Preparation of ethylene glycol-1,2-ditosylate (1) Add 17 g of toluenesulfonyl chloride (TsCl) (F.W.=190.65, 0.089 mol) into conical flask (A) with 20 ml of pyridine.

(2) Add 1.1 ml of ethylene glycol (F.W.=62.07, 0.018 mol) into conical flask (B) with 30 ml of pyridine.

(3) Pour solution of conical flask (A) into conical flask (B) under the temperature of dry ice-acetone bath (−30° C. approximately) and then put the flask under −18° C. promptly for react two to three days.

(4) After complete reaction, pour the reactant in conical flask (B) into 500 ml beaker with ice water and cracked ice; white solid substance will appear after stirring.

(5) Add optimal 1N HCl into beaker above-mentioned and adjust pH to 6~7.

(6) Filter and collect white solid substance, then re-crystallize in mixture of methylene chloride and normal hexane to yield 80% of 5.33 g ethylene glycol-1,2-ditosylate.

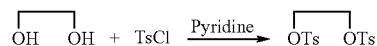

Formula 2: Reaction of synthetic ethylene glycol-1,2-ditosylate

2. Preparation of t-BOC-(O-tosyloxyethyl)-L-Tyr-OBzl

Following is the synthetic process of using t-BOC-L-Tyr-OBzl as a raw material (Formula 2):

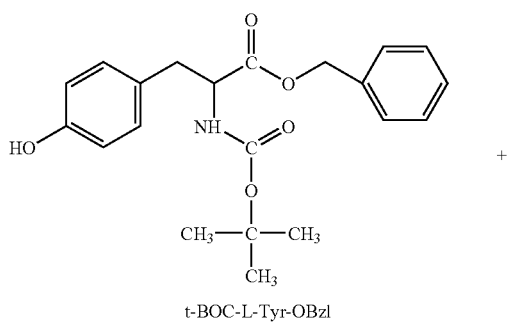

t-BOC-L-Tyr-OBzl

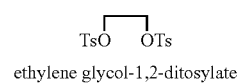

ethylene glycol-1,2-ditosylate

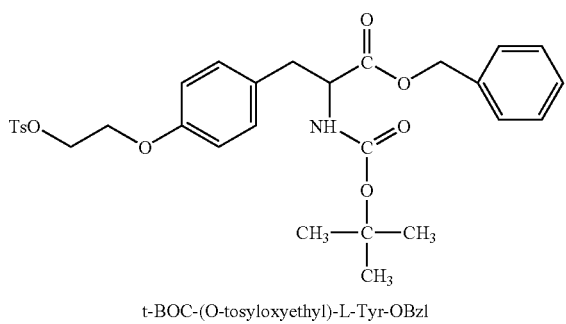

t-BOC-(O-tosyloxyethyl)-L-Tyr-OBzl

Formula 3: The synthetic reaction of t-BOC-(O-tosyloxyethyl)-L-Tyr-OBzl from t-BOC-L-Tyr-OBzl (1) Add 450 mg of N-tert-butyloxycarbonyl-L-tyrosine benzylester (t-BOC-L-Tyr-OBzl) (F.W.=361, 1.24 mmol) into 50 ml of round bottomed flask contains 20 mg potassium carbonate and 1.384 g ethylene glycol-1,2-ditosylate (F.W.=370.35, 3.73 mmol); then add 25 ml anhydrous acetonitrile at 90° C. and stir for 3.5 hours.

(2) After complete the reaction, remove solvent with rotavapor and extract with chloroform (5 ml x3). Harvest chloroform extract and remove solvent under negative pressure.

(3) Dissolve solid residue with minimum amount of methylene chloride, then perform silica gel chromatography (add 0.1% triethylamine in eluent) for purification. The initial condition of mobile phase is 100% $CH_2Cl_2$; after remove un-react ethylene glycol-1,2-ditosylate the condition of mobile phase change to $CH_2Cl_2/CHCl_3=1/1$, the crude product then eluted. Dry crude product under reduced pressure and obtain the solid crude product.

(4) Dissolve crude product with minimum volume solution of $CH_2Cl_2:CHCl_3=8/2$, then perform silica gel chromatography (add 0.1% triethylamine in eluent) for purification; the initial condition of mobile phase is $CH_2Cl_2/CHCl_3=8/2$ (another 0.1% triethyl amine is added); light yellow oil-like substance (398 mg) of pure N-tert-butyloxycarbonyl-(O-tosyloxyethyl)-L-tyrosine benzylester (t-BOC-(O-tosyloxyethyl)-L-Tyr-OBzl) is eluted; re-crystallize in dichloromethane and n-hexane to yield 60.1% of white solid substance, melt point 85~86° C.

(5) Nuclear Magnetic Resonance (NMR): Dissolve 20 mg of t-BOC-(O-tosyloxyethyl)-L-Tyr-OBzl in 0.6 ml $CDCl_3$, then determine its $^1$H-NMR spectrum (Formula 3). $^1$H NMR ($CDCl_3$) δ7.80 (d, 2H, J=8.4 Hz, Haryl), 7.31 (m, 7H, Haryl), 6.89 (d, 2H, J=8.4 Hz, Haryl), 6.62 (d, 2H, J=8.4 Hz, Haryl), 5.15 (d, 1H, 12.2 Hz, CH of benzyl), 5.08 (d, 1H, 12.2 Hz, CH of benzyl), 4.92 (d, 1H, J=8.0 Hz, NH), 4.54 (m, 1H, CH), 4.33 (t, 2H, J=4.6 Hz, $CH_2$), 4.07 (t, 2H, J=4.6 Hz, $CH_2$), 2.99 (d, 2H, J=5.8 Hz, $CH_2$ of Tyr), 2.43 (s, 3H, $CH_3$ of toluene), 1.39 (s, 9H, $CH_3$ of t-BOC).

(6) Elemental analysis: The formula of t-BOC-(O-tosyloxyethyl)-L-Tyr-OBzl is $C_{30}H_{35}NO_8S$, the calculated value of elemental analysis is: C, 63.27; H, 6.15; N, 2.46. The actual value is: C, 63.34; H, 5.62; N, 2.33.

The invention claimed is:

1. A method of producing a precursor of $^{18}F$-labeled O-(2-[$^{18}F$]fluoroethyl)-L-Tyrosine, which has the following chemical structure:

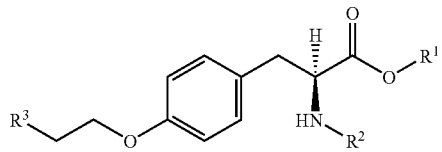

wherein $R^1$ is a protective group for the carboxyl functional group and represents an arylalkyl group;

$R^2$ is a protective group for the amino group and represents a carboxyl group; and $R^3$ acts as a leaving group and represents a p-tosyloxy, methane sulfonyloxy or trifluoromethane sulfonyloxy or bromine, said method comprising step (a) preparation of ethylene glycol-1,2-ditosylate and step (b) preparation of t-BOC-(O-tosyloxyethyl)-L-TYr-OBzl, wherein step (a) comprises:

(1) adding toluenesulfonyl chloride (TsCl) to pyridine to form a first solution;

(2) adding ethylene glycol to pyridine to form a second solution, (3) pouring the first solution into the second solution under the temperature of dry ice-acetone bath (−30° C. approximately) to form a mixture and then keeping the mixture under −18° C. promptly for reacting two to three days;

(4) pouring the mixture from (3) into ice water and cracked ice; then stirring until a white solid substance appears;

(5) adding optimal 1N HCl into the white solid substance and adjusting the pH of the resultant solution to 6~7; and (6) filtering and collecting the white solid substance then re-crystallizing the white solid substance in a mixture of methylene chloride and normal hexane to yield ethylene glycol-1,2-ditosylate, and step (b) comprises:

(1) adding N-tert-butyloxycarbonyl-L-tyrosine benzylester (t-BOC-L-Tyr-OBzl) to a mixture of potassium carbonate and ethylene glycol-1,2-ditosylate; then adding anhydrous acetonitrile at 90° C. and stirring the resultant mixture for 3.5 hours, (2) removing the solvent from the mixture from (1) with rotavapor and extracting it with chloroform (5 ml x3); harvesting the chloroform extract and removing the solvent under negative pressure to yield a solid residue;

(3) dissolving the solid residue with methylene chloride then performing silica gel chromatography (with addition of 0.1% triethylamine in eluent) for purification, wherein the initial condition of mobile phase is 100% $CH_2Cl_2$ and after removing unreacted ethylene glycol-1,2-ditosylate the condition of mobile phase is changed to $CH_2Cl_2/CHCl_3=1/1$, a crude product being eluted;

(4) drying the crude product under reduced pressure to obtain a solid crude product;

(5) dissolving the solid crude product with a minimum volume of solution $CH_2Cl_2:CHCl_3=8/2$, then performing silica gel chromatography (with addition of 0.1% triethylamine in eluent) for purification, wherein the initial condition of mobile phase is $CH_2Cl_2/CHCl_3=8/$ 2, (with another addition of 0.1% triethylamine) a light yellow oil-like substance of pure N-tert-butyloxycarbonyl-(O-tosyloxyethyl)-L-tyrosine benzylester (t-BOC-(O-tosyloxyethyl)-L-Tyr-OBzl) being eluted; and (6) re-crystallizing the product from (5) in dichloromethane and n-hexane to yield a white solid substance.

* * * * *